US012729296B2

(12) United States Patent
Gorgerin et al.

(10) Patent No.: US 12,729,296 B2
(45) Date of Patent: Sep. 8, 2026

(54) POLYPROPYLENE BLEND

(71) Applicant: INEOS EUROPE AG, Vaud (CH)

(72) Inventors: Michel Gorgerin, Masnuy-Saint-Jean (BE); Annick Libotte, Nivelles (BE)

(73) Assignee: INEOS EUROPE AG, Vaud (CH)

( * ) Notice: Subject to any disclaimer, the term of this patent is extended or adjusted under 35 U.S.C. 154(b) by 620 days.

(21) Appl. No.: 18/258,751

(22) PCT Filed: Dec. 16, 2021

(86) PCT No.: PCT/EP2021/086310
§ 371 (c)(1),
(2) Date: Jun. 21, 2023

(87) PCT Pub. No.: WO2022/136131
PCT Pub. Date: Jun. 30, 2022

(65) Prior Publication Data

US 2024/0043673 A1 Feb. 8, 2024

(30) Foreign Application Priority Data

Dec. 21, 2020 (EP) .................................... 20216031

(51) Int. Cl.

*C08L 23/16* (2006.01)
*A61M 5/31* (2006.01)
*C08K 5/098* (2006.01)
*C08L 23/0807* (2025.01)
*C08L 23/14* (2006.01)

(52) U.S. Cl.

CPC ........... *C08L 23/16* (2013.01); *A61M 5/3129* (2013.01); *C08K 5/098* (2013.01); *C08L 23/0815* (2013.01); *C08L 23/14* (2013.01); *C08L 2203/02* (2013.01); *C08L 2205/025* (2013.01); *C08L 2205/24* (2013.01)

(58) Field of Classification Search

CPC combination set(s) only.
See application file for complete search history.

(56) References Cited

U.S. PATENT DOCUMENTS

2020/0224017 A1* 7/2020 Huang .................... C08L 23/14
2020/0385556 A1* 12/2020 Gahleitner ............ C08F 210/06

FOREIGN PATENT DOCUMENTS

CA 2254537 A1 * 6/1999 .......... C08L 23/0815
EP 0089691 A2 9/1983
EP 0699213 A1 3/1996
EP 0735089 A2 10/1996
EP 814127 A1 * 12/1997
EP 0847420 A1 6/1998
EP 3912792 A1 * 11/2021 ............ B29C 49/08
WO 9428032 A1 12/1994
WO 9708238 A1 3/1997
WO 0214045 A1 2/2002
WO 2016091924 A1 6/2016
WO 2016200335 A1 12/2016
WO 2017005867 A1 1/2017
WO WO-2017076412 A1 * 5/2017 ............... C08K 7/14

OTHER PUBLICATIONS

International Search Report and Written Opinion of the ISA for PCT/EP2021/086310 dated Mar. 16, 2022, 10 pages.
Jun. 13, 2023 International Preliminary Report on Patentability issued in International Patent Application No. PCT/EP2021/086310, pp. 1-8.

* cited by examiner

*Primary Examiner* — Marc S Zimmer
(74) *Attorney, Agent, or Firm* — Nixon & Vanderhye PC

(57) ABSTRACT

A composition is disclosed comprising a blend of 90-99 wt %, based on the blend, of a random propylene copolymer having an melt flow rate (MFR 230° C./2.16 kg) of 15-40 g/10 min and containing 1.5-2.5 wt % ethylene, and 1-10 wt %, based on the blend, of an ethylene based plastomer having a density of 860-915 kg/m$^3$ and an $MI_2$ (190° C./2.16 kg) of 0.5 to 25 g/10 min. The blend preferably has an MFR of 15-35 g/10 min and a flexural modulus of 700-1300 MPa.

19 Claims, No Drawings

POLYPROPYLENE BLEND

This application is the U.S. national phase of International Application No. PCT/EP2021/086310 filed Dec. 16, 2021 which designated the U.S. and claims priority to EP patent application No. 20216031.3 filed Dec. 21, 2020, the entire contents of each of which are hereby incorporated by reference.

The present invention concerns polypropylene compositions suitable for fabrication into rigid articles such as syringe barrels. More particularly, the invention concerns blends of a random propylene copolymer and a small amount of an ethylene based plastomer.

Syringe barrels of the type commonly used in medical applications require a particular balance of rigidity, impact resistance and optical properties, and the compositions from which they are made must also be suited for the injection moulding process as well as being suitable for sterilisation by radiation. Ionizing radiation, particularly gamma radiation, is known to degrade some polymers.

It is well known to construct containers useful as medical devices, and particularly syringes, out of polypropylene. For example WO 02/14045 discloses injection moulded compositions for syringe barrels made from random propylene ethylene copolymers containing up to 5 wt % ethylene and having an MFR in the range 2-100 g/10 min, more particularly 15-30 g/10 min.

It is also well known to incorporate into such polypropylene compositions other components in order to improve the properties. WO 02/14045 itself discloses the addition of slip agents such as polyethylene wax to improve operation of the syringe without adversely impacting the optical properties. EP 735089A discloses the addition of unsaturated aliphatic compounds such as safflower oil to improve the radiation stability of polypropylene compositions used in medical devices.

It is also known to blend polypropylene with other polymers such as polyethylenes in order to obtain properties suitable for different applications. WO 2016/091924 discloses films made from a blend of 75-98 wt % of a polypropylene random copolymer with 2-15 wt % of an ethylene-based plastomer having a density below 915 kg/m$^3$ and an $MI_2$ of 2-30 g/10 min.

EP 847420A discloses blends of up to 99 wt % of a polypropylene homopolymer or copolymer with at least 1 wt % of polyethylene produced by single site catalysis and having a narrow molecular weight distribution. The polypropylene is preferably a homopolymer, but random copolymers are also mentioned, although amounts of comonomer are not disclosed, and nor is the MFR of the polypropylene. Examples of the polyethylene have densities in the range 865-910 kg/m$^3$ and $MI_2$ from 1.1-10 g/10 min, and are blended with a polypropylene homopolymer having an MFR of 1 g/10 min. The blends are said to be resistant to degradation by sterilising radiation and to have good optical properties. Applications disclosed include medical devices such as syringe barrels. However, due to the use of propylene homopolymers in the blends, they have relatively high stiffness and haze values. This can be a disadvantage for syringe barrels which need a certain level of flexibility in order to accommodate the plunger and provide a tight seal between the plunger and the barrel. Low haze is also desired to enable the precise determination of the volume to be measured in the syringe.

WO 2016/200335 discloses blends of a propylene copolymer or terpolymer and 2-15 wt % of an elastomer having a density of 860-899 kg/m$^3$, together with an organic peroxide, for use in moulded articles such as containers or syringes. The compositions are said to provide improved impact strength compared with equivalent compositions where the organic peroxide is absent.

Whilst the blending of polypropylene with other components can improve radiation tolerance, it is also important to maintain physical properties such as impact resistance and stiffness as well as optical properties such as clarity and haze. Additionally, processability during the injection moulding process is important. For example, the lower the crystallisation temperature, the longer the cooling step required and hence the longer the cycle time, which obviously reduces productivity.

We have found a polypropylene blend which has an excellent balance of good impact resistance, rigidity and haze as well as a high crystallisation temperature which permits a fast cycle time during injection moulding.

Accordingly in a first aspect the present invention provides a composition comprising a blend of 90-99 wt %, based on the blend, of a random propylene copolymer having an melt flow rate (MFR 230° C./2.16 kg) of 15-40 g/10 min and containing 1.5-2.5 wt % ethylene, and 1-10 wt %, based on the blend, of an ethylene based plastomer having a density of 860-915 kg/m$^3$ and an $MI_2$ (190° C./2.16 kg) from 0.5 to 25 g/10 min.

Both MFR (230° C./2.16 kg) and $MI_2$ (190° C./2.16 kg) are determined according to ISO 1133.

The blend preferably comprises 92-98 wt %, more preferably 93-97 wt %, based on the blend, of the propylene copolymer and 2-8 wt %, more preferably 3-7 wt %, based on the blend, of the plastomer. Most preferred ranges of propylene copolymer and plastomer are 94-96 wt % and 4-6 wt % respectively.

The blend preferably has an MFR of 15 to 35 g/10 min, more preferably 17 to 33 g/10 min, and most preferably 19 to 29 g/10 min.

The blend preferably has a flexural modulus of 700-1300 MPa, preferably 800-1200 MPa and more preferably 900-1100 MPa.

When no nucleating agent is present, the blend preferably has a melting temperature $T_m$ of at least 146° C., more preferably at least 147° C. It preferably has a crystallisation temperature Tc of at least 107° C., more preferably at least 108° C. It preferably has a haze of less than 50%, more preferably less than 45%.

The blend preferably contains less than 0.001 wt % (based on total polymer) of peroxides or peroxide residues, and is preferably free of peroxides or peroxide residues.

Random Propylene Copolymer

The random propylene copolymer comprises units derived from propylene and ethylene and/or another $C_4$ to $C_{20}$ α-olefin, preferably 1-butene, 1-pentene, 1-hexene, 1-heptene, 1-octene, 1-nonene or 1-decene. Ethylene and/or 1-butene are preferred. Most preferably the copolymer is a propylene-ethylene copolymer.

The MFR (MFR 230° C./2.16 kg) of the random propylene copolymer is determined according to ISO1133, and is preferably from 20 to 30 g/10 min, more preferably in the range of 22 to 28 g/10 min.

The random propylene copolymer preferably has an XCS content in the range 3-10 wt %, preferably 4-9 wt %.

A first preferred random propylene copolymer has an MFR of 15 to 40 g/10 min and an XCS content in the range 3-10 wt %.

A second preferred random propylene copolymer has an MFR of 15 to 40 g/10 min and an XCS content in the range 4-9 wt %.

Random propylene copolymers are widely available commercially. They can be produced by polymerization in the presence of any conventional coordination catalyst system including Ziegler-Natta and single site catalysts such as metallocenes, and in any conventional polymerisation process such as gas phase, slurry and propylene bulk processes known in the art.

A preferred polymerisation process is a fluidised bed gas phase process comprising a single reactor or two reactors in series, in which the same copolymer is made in both reactors. Polymerization of propylene and comonomer is conducted in the first reactor. Hydrogen is used to obtain the desired MFR value. The catalyst system components are added at a rate to obtain the desired rate of polymerization.

The polymer powder containing active catalyst residues is intermittently transferred to a depressurization vessel to remove unreacted monomer and other gaseous components. The depressurization vessel is pressurized with nitrogen to convey the polymer powder into the second reactor for further polymerization. Further propylene, comonomer and hydrogen are added in a ratio to obtain the desired composition. The polymer powder is intermittently removed from the second reactor for subsequent removal of all volatile materials followed by compounding to obtain the target composition in the form of pellets.

The random propylene copolymer may optionally be nucleated with at least one α-nucleating agent. Generally any α-nucleating agent can be used. Examples of suitable α-nucleating agents include (i) salts of monocarboxylic acids and polycarboxylic acids, e.g. sodium benzoate or aluminum tert-butylbenzoate, (ii) dibenzylidenesorbitol (e.g. 1,3:2,4 dibenzylidenesorbitol) and C18-C-alkyl-substituted dibenzylidenesorbitol derivatives, such as methyldibenzylidenesorbitol, ethyldibenzylidenesorbitol or dimethyldibenzylidenesorbitol (e.g. 1,3:2,4 di(methylbenzylidene) sorbitol), nonitol,1,2,3,-trideoxy-4,6:5,7-bis-O-[(4-propylphenyl)methylene]-nonitol, (iii) salts of diesters of phosphoric acid, e.g. sodium 2,2'-methylenebis(4,6,-di-tert-butylphenyl)phosphate or aluminium-hydroxy-bis[2,2'-methylene-bis(4,6-di-t-butylphenyl)phosphate], and (iv) vinylcycloalkane polymer and vinylalkane polymers.

Any nucleating agent is preferably present in the random propylene copolymer in an amount of from 10 to 10000 ppm, preferably from 200 to 5000 ppm based on the weight of the copolymer.

Ethylene Based Plastomer

The ethylene based plastomer is a copolymer of ethylene and a $C_3$-$C_{10}$ alpha-olefin. Suitable $C_3$-$C_{10}$ alpha-olefins include 1-propylene, 1-butene, 1-hexene and 1-octene, preferably 1-butene or 1-hexene and most preferably 1-hexene.

The comonomer content of the ethylene based plastomer is typically between 4 and 7 mol %, preferably between 4.5 and 6.5 mol % and most preferably between 5.0 and 6.0 mol %.

The plastomer preferably has a density in the range of 870-910 kg/m$^3$, more preferably in the range of 890-910 kg/m$^3$ and most preferably in the range 898-905 kg/m$^3$.

The plastomer preferably has an $MI_2$ (ISO 1133; 190° C.; 2.16 kg) in the range of 0.5-15 g/10 min, preferably in the range of 0.5-5 g/10 min and more preferably in the range of 0.5-3.0 g/min. Particularly preferred ranges are 0.3-2.5 g/10 min and 1.0 to 1.6 g/10 min.

The plastomer preferably has a molecular weight distribution (Mw/Mn) in the range 3 to 5, more preferably 3.2 to 4.5 and most preferably 3.4 to 4.5.

A first preferred plastomer has a density in the range 890-910 kg/m$^3$ and an $MI_2$ in the range of 0.5-3.0 g/min, preferably 0.3-2.5 g/10 min and more preferably 1.0 to 1.6 g/10 min. It preferably also has a molecular weight distribution (Mw/Mn) in the range 3 to 5.

A second preferred plastomer has a density in the range 898-905 kg/m$^3$ and an $MI_2$ in the range 0.5-3.0 g/min, preferably 0.3-2.5 g/10 min and more preferably 1.0 to 1.6 g/10 min. It preferably also has a molecular weight distribution (Mw/Mn) in the range 3 to 5.

Furthermore suitable ethylene based plastomers have a glass transition temperature Tg (measured with DMTA according to ISO 6721-7) of below −25° C., preferably below −30° C., more preferably below −35° C.

Suitable plastomers our those disclosed in our copending application WO 2017/005867.

The plastomer may suitably be prepared by a process such as that disclosed in WO 2017/005867, using a metallocene catalyst system which is preferably a monocyclopentadienyl metallocene complex having a 'constrained geometry' configuration together with a suitable activator as described in the earlier application.

The plastomer is most suitably prepared in a gas phase process, and most preferably in a gas phase process operating in a fluidised bed. Particularly preferred gas phase processes are those operating in "condensed mode" as described in EP 89691 and EP 699213, the latter being a particularly preferred process. By "condensed mode" is meant the "process of purposefully introducing a recycle stream having a liquid and a gas phase into a reactor such that the weight percent of liquid based on the total weight of the recycle stream is typically greater than about 2.0 weight percent".

The Blend

One preferred blend comprises the first preferred random propylene copolymer defined above, having an MFR of 15 to 40 g/10 min and an XCS content in the range 3-10 wt %, in combination with a plastomer having a density in the range 890-910 kg/m$^3$ and an $MI_2$ in the range of 0.5-3.0 g/min, preferably 0.3-2.5 g/10 min and more preferably 1.0 to 1.6 g/10 min.

Another preferred blend comprises the first preferred random propylene copolymer defined above, having an MFR of 15 to 40 g/10 min and an XCS content in the range 3-10 wt %, in combination with a plastomer having a density in the range 898-905 kg/m$^3$ and an $MI_2$ in the range of 0.5-3.0 g/min, preferably 0.3-2.5 g/10 min and more preferably 1.0 to 1.6 g/10 min.

A further preferred blend comprises the second preferred random propylene copolymer defined above, having an MFR of 15 to 40 g/10 min and an XCS content in the range 4-9 wt %, in combination with a plastomer having a density in the range 890-910 kg/m$^3$ and an $MI_2$ in the range of 0.5-3.0 g/min, preferably 0.3-2.5 g/10 min and more preferably 1.0 to 1.6 g/10 min.

A further preferred blend comprises the second preferred random propylene copolymer defined above, having an MFR of 15 to 40 g/10 min and an XCS content in the range 4-9 wt %, in combination with a plastomer having a density in the range 898-905 kg/m$^3$ and an $MI_2$ in the range of 0.5-3.0 g/min, preferably 0.3-2.5 g/10 min and more preferably 1.0 to 1.6 g/10 min.

The blend can be produced by any suitable melt mixing process at temperatures above the melting point of the respective blend. Typical devices for performing said melt mixing process are twin screw extruders, single screw extruders optionally combined with static mixers, chamber kneaders like Farrel kneaders, Banbury type mixers and reciprocating co-kneaders like Buss co-kneaders. Preferably, the melt mixing process is carried out in a twin screw extruder with high intensity mixing segments and preferably at a temperature of 170 to 270° C., more preferably of 180 to 250° C.

It is also possible to produce the blend of the present invention by dry-blending in a suitable mixing equipment, like horizontal and vertical agitated chambers, tumbling vessels, and Turbula mixers, as long as sufficient homogeneity is obtained.

The composition of the invention which comprises the blend may also contain other additives, as is well known in the art. Typical additives used in such compositions are listed below.

Examples of antioxidants are sterically hindered phenols (such as CAS No. 6683-19-8, also sold as Irganox 1010 FF™ by BASF), phosphorous based antioxidants (such as CAS No. 31570-04-4, also sold as Hostanox PAR 24 (FF)™ by Clariant, or Irgafos 168 (FF)™ by BASF), sulphur based antioxidants (such as CAS No. 693-36-7, sold as Irganox PS-802 FL™ by BASF), nitrogen-based antioxidants (such as 4,4'-bis(1,1'-dimethylbenzyl)diphenylamine), or antioxidant blends.

Examples of acid scavengers are calcium stearates, sodium stearates, zinc stearates, magnesium and zinc oxides, synthetic hydrotalcite (e.g. SHT, CAS-no. 11097-59-9), lactates and lactylates, as well as calcium and zinc stearates.

Examples of antiblocking agents are natural silica such as diatomaceous earth (such as CAS-no. 60676-86-0 (SuperfFloss™), CAS-no. 60676-86-0 (SuperFloss E™), or CAS-no. 60676-86-0 (Celite 499™)), synthetic silica (such as CAS-no. 7631-86-9, CAS-no. 7631-86-9, CAS-no. 7631-86-9, CAS-no. 7631-86-9, CAS-no. 7631-86-9, CAS-no. 7631-86-9, CAS-no. 112926-00-8, CAS-no. 7631-86-9, or CAS-no. 7631-86-9), silicates (such as aluminum silicate (Kaolin) CAS-no. 1318-74-7, sodium aluminum silicate CAS-no. 1344-00-9, calcined kaolin CAS-no. 92704-41-1, aluminum silicate CAS-no. 1327-36-2, or calcium silicate CAS-no. 1344-95-2), synthetic zeolites (such as sodium calcium aluminosilicate hydrate CAS-no. 1344-01-0, CAS-no. 1344-01-0, or sodium calcium aluminosilicate, hydrate CAS-no. 1344-01-0).

Examples of UV-stabilisers are, for example, bis-(2,2,6,6-tetramethyl-4-piperidyl)-sebacate (CAS 52829-07-9, Tinuvin 770); 2-hydroxy-4-n-octoxy-benzophenone (CAS 1843-05-6, Chimassorb 81).

Examples of nucleating agents are sodium benzoate (CAS 532-32-1) and 1,3:2,4-bis(3,4-dimethylbenzylidene)sorbitol (CAS 135861-56-2, Millad 3988).

The above additives are typically incorporated in the composition in quantities of 100-10000 ppm for each additive.

When a nucleating agent is present in the composition, the composition preferably has a melting temperature $T_m$ of at least 149° C., more preferably at least 150° C., It preferably has a crystallisation temperature Tc of at least 120° C., more preferably at least 122° C. It preferably has haze of less than 20%, more preferably less than 18%.

The compositions of the invention are suitable for fabrication into articles, particularly rigid articles such as medical devices, which can also be subject to sterilisation procedures known in the art. A particularly preferred application is syringe barrels.

EXAMPLES

The meanings of the symbols used in these examples and the units expressing the properties mentioned and the methods for measuring these properties are explained below.

Melt Index

The melt flow rate of the polypropylene (MFR) and the melt index of the polyethylene ($MI_2$) are determined according to ISO1133 at temperatures of 230° C. (MFR) and 190° C. ($MI_2$) under a load of 2.16 kg and are indicated in g/10 min.

Density

Density of the polyethylene was measured according to ISO 1183-1 (Method A) and the sample plaque was prepared according to ASTM D4703 (Condition C) where it was cooled under pressure at a cooling rate of 15° C./min from 190° C. to 40° C.

Melting Temperature (Tm) and Crystallisation Temperature (Tc)

These were measured by Differential Scanning Calorimetry (DSC) with a cooling rate of 10° C./min.

Flexural Modulus

Flexural modulus was measured according to ISO 178 at 23° C. on ISO 1A plaques of 10 mm width and 4 mm thickness, injection moulded according to ISO 294-1.

Haze

Haze was measured using a “Haze-Guard plus” haze meter from BYK Garder referred to in ASTM-D1003.

Xylene Cold Soluble Fraction (XCS)

XCS was determined at 25° C. according to ISO 16152 by putting 3 g of polymer in a solution in 200 ml of metaxylene at boiling temperature, cooling the solution to 25° C. by immersion in a water bath and maintaining the solution at that temperature for 1 hour, and filtering the soluble fraction at 25° C. on filter paper.

Resilience

Resilience was measured according to ISO 6603 at room temperature using an instrumented drop tower. A striker with a diameter of 20 mm and a total weight of 21.03 kg was dropped from a height of 1 metre, giving an impact speed of 4.43 m/s and an impact energy of 206 J.

Random Propylene Copolymer

Copolymers having ethylene contents ranging from 1.6 to 3.0 wt % were made in a single reactor continuous fluidised bed gas phase polymerisation reactor system having a vertical cylindrical section of 2.7 m height and 0.5 m diameter.

Polymerisation was initiated by the introduction of a high activity supported titanium containing Ziegler-Natta catalyst component commercially available from Grace under the trade name C602 through a liquid propylene-flushed catalyst addition nozzle. A mixture of selectivity control agent (SCA), commercially available from Grace under the trade name D-9600, plus trialkylaluminum (TEA) co-catalyst in hexane was fed separately to the first reactor through a different liquid propylene-flushed addition nozzle to obtain a Al/SCA ratio of about 3 and a Al/Ti ratio of about 160. Hydrogen, ethylene and propylene were fed to the reactor through separate mass-flow meters in order to achieve the desired powder melt flow rate (MFR) and ethylene content. The reactor temperature was maintained at 57° C.

Polymer was continuously with drawn from the reactor and subjected to a reduction in pressure to remove all volatile materials, followed by a final degassing step. The polymer powder was then homogenised in an Ancheschi F6950 cylinder-conical discontinuous homogeniser. The properties of the random propylene copolymer powders are given in Tables 1 and 2.

Ethylene-Based Plastomer

The plastomer was made as described in the Examples of WO 2017/005867 in a fluidized bed gas phase reactor of 5 m diameter, with a vertical cylindrical section of 15.8 m. The resulting polymer powder was pelletized in an extruder together with 800 ppm Irgafos 168 and 275 ppm Irganox 1010. The properties of the ethylene plastomer pellets are given in Tables 1 and 2.

The Composition

The random propylene copolymer powder and plastomer pellets were blended in a Papenmeier mixer (volume 17.5 $dm^3$, rotation speed 1500 tr/min for 5 mins), together with additives in the amounts given in Table 1 and 2. The additives used were the following:

IRGANOX 1010 (tetrakis-(methylene-(3,5-di-(tert)-butyl-4-hydrocinnamate))-methane available from BASF IRGAFOS PEP-Q (tetrakis(2,4-di-tert-butylphenyl)[1,1-biphenyl]-4,4'diylbisphosphonite available from BASF IRGAFOS 168 (tris(2,4-di-tert.-butylphenyl)phosphite) available from BASF MILLAD 3988 (1,3:2,4-bis(3,4-dimethylbenzylidene) sorbitol) available from Milliken Chemicals DHT-4A (hydrotalcite) available from Kyowa Chemical.

The homogenized mixture was then pelletized in an APV 19TC25 extruder. The barrel temperature used was 210° C., the screw speed was 300 rpm and the throughput was 5 kg/h. The barrel diameter D was 19 mm and the barrel length to diameter (LID) ratio was 25.

Examples labelled "CE" below are comparative examples.

TABLE 1

| EXAMPLE | CE1 | 2 | 3 | CE4 | CE5 | CE6 |
|---|---|---|---|---|---|---|
| Random ethylene-propylene copolymer | | | | | | |
| MFR (g/10 min) | | 24.0 | | | 23.3 | |
| C2 content (wt %) | | 2.0 | | | 2.8 | |
| XCS (wt %) | | 7.5 | | | nm | |
| Amount (wt %) | 100 | 98 | 95 | 100 | 98 | 95 |
| Ethylene-based plastomer | | | | | | |
| Amount (wt %) | 0 | 2 | 5 | 0 | 2 | 5 |
| $MI_2$ (g/10 min) | | | | 1.3 | | |
| Density ($kg/m^3$) | | | | 902 | | |
| Additives added during blending | | | | | | |
| Millad 3988 (ppm) | | | 1800 | | | |
| Irganox 1010 (ppm) | | | 500 | | | |
| Irgafos PEPQ (ppm) | | | 500 | | | |
| Ca Stearate (ppm) | | | 1000 | | | |
| Composition | | | | | | |
| MFR (g/10 min) | 21.0 | 21.3 | 19.6 | 21.5 | 20.4 | 19.9 |
| Flexural modulus (MPa) | 1210 | 1180 | 1133 | 1051 | 1029 | 997 |
| Tm (° C.) | 151.5 | 151.6 | 151.4 | 148.6 | 148.3 | 148.5 |
| Tc (° C.) | 122.6 | 122.3 | 122.4 | 119.6 | 119.7 | 119.7 |
| Haze (%) | 14.9 | 14.9 | 16.6 | 13.2 | 14.1 | 15.1 |
| Resilience (J/mm) | 7.7 | 10.56 | 11.8 | 12.25 | 11.67 | 12.27 |

nm = not measured

A comparison of comparative Example CE1 (which contains no plastomer) with Examples 2 and 3 shows that the pure copolymer has relatively poor resilience. Resilience is typically improved by increasing the comonomer content, but that reduces the crystallisation temperature and rigidity. However it can be seen that inventive Examples 2 and 3 have much better resilience, but still have essentially the same crystallisation temperature and similar flexural modulus.

However in Examples CE4-CE6 no such improvement in resilience is observed upon addition of the plastomer, indicating that there is an optimum level of comonomer in the random copolymer.

TABLE 2

| EXAMPLE | CE7 | 8 | 9 | CE10 | CE11 | CE12 | CE13 | CE14 | CE15 |
|---|---|---|---|---|---|---|---|---|---|
| Random ethylene-propylene copolymer | | | | | | | | | |
| MFR (g/10 min) | | 24.0 | | | 23.3 | | | 20.6 | |
| C2 content (wt %) | | 2.0 | | | 2.8 | | | 3.0 | |
| XCS (wt %) | | 7.5 | | | nm | | | nm | |
| Amount (wt %) | 100 | 98 | 95 | 100 | 98 | 95 | 100 | 98 | 95 |
| Ethylene-based plastomer | | | | | | | | | |
| Amount (wt %) | 0 | 2 | 5 | 0 | 2 | 5 | 0 | 2 | 5 |
| $MI_2$ (g/10 min) | | | | | 1.3 | | | | |
| Density ($kg/m^3$) | | | | | 902 | | | | |
| Additives added during blending | | | | | | | | | |
| Irgafos 168 (ppm) | | | | | 500 | | | | |
| Irganox 1010 (ppm) | | | | | 500 | | | | |
| DHT-4A (ppm) | | | | | 400 | | | | |
| Composition | | | | | | | | | |
| MFR (g/10 min) | 23 | 21.8 | 19.7 | 20.8 | 20.5 | 18.9 | 18.8 | 18.3 | 17 |
| Flexural modulus (MPa) | 1070 | 1044 | 1013 | 941 | 926 | 915 | 856 | 850 | 840 |
| Tm (° C.) | 147.9 | 147.4 | 147.8 | 144.3 | 144.1 | 144.0 | 142.2 | 142.4 | 141.9 |
| Tc (° C.) | 110.3 | 108.5 | 109.9 | 106.9 | 106.3 | 105.4 | 104.9 | 103.7 | 103.4 |
| Haze (%) | 43 | 43 | 41 | 41 | 41 | 40 | 39 | 39 | 40 |
| Resilience (J/mm) | 3.5 | 9.6 | 12 | 11.8 | 13.1 | 14.1 | 11.9 | 14.7 | 13.7 |

nm = not measured

Unlike the compositions of Table 1, those of Table 2 do not contain a nucleating agent. It can be seen that in the absence of a nucleating agent the blend has, as expected, a higher haze value and higher crystallisation temperature, but a comparison of Examples 8 and 9 with CE7 shows an improvement in resilience. Comparative Examples CE11-CE15 show that at higher ethylene content of the random propylene copolymer the crystallisation temperature and the flexural modulus is low.

The invention claimed is:

1. Composition comprising a blend of 90-99 wt %, based on the blend, of a random propylene copolymer having a melt flow rate (MFR 230° C./2.16 kg) of 15-40 g/10 min, containing 1.5-2.5 wt % ethylene, and having an XCS content of 3-10 wt %, and 1-10 wt %, based on the blend, of an ethylene based plastomer having a density of 860-915 kg/m$^3$ and an $MI_2$ (190° C./2.16 kg) of 0.5-5 g/10 min.

2. Composition according to claim 1, which comprises 92-98 wt %, based on the blend, of the random propylene copolymer and 2-8 wt %, based on the blend, of the plastomer.

3. Composition according to claim 2, which comprises 94-96 wt % of the random propylene copolymer and 4-6 wt % of the plastomer.

4. Composition according to claim 1, which has an MFR of 15 to 35 g/10.

5. Composition according to claim 1, which has a flexural modulus of 700-1300 MPa.

6. Composition according to claim 1, wherein the ethylene based plastomer has a density in the range 870-910 kg/m$^3$.

7. Composition according to claim 1, wherein the random propylene copolymer has an MFR of 15 to 40 g/10 min and an XCS content in the range 3-10 wt %, and the ethylene-based plastomer has a density in the range 898-905 kg/m$^3$ and an $MI_2$ in the range of 0.5-3.0 g/min.

8. Composition according to claim 1, wherein the random propylene copolymer has an XCS content of 4-9 wt %.

9. Composition according to claim 1, wherein the random propylene copolymer has an MFR of 20 to 30 g/10 min.

10. Composition according to claim 1, wherein the random propylene copolymer contains at least one α-nucleating agent.

11. Composition according to claim 1, wherein the ethylene based plastomer is a copolymer of ethylene and a $C_3$-$C_{10}$ alpha-olefin.

12. Composition according to claim 1, wherein the comonomer content of the ethylene based plastomer is 4 to 7 mol %.

13. Composition according to claim 1, wherein the ethylene based plastomer has a molecular weight distribution (Mw/Mn) in the range 3 to 5.

14. Composition according to claim 1, wherein the ethylene based plastomer has a glass transition temperature Tg (measured with DMTA according to ISO 6721-7) of below −25° C.

15. An article comprising the composition as defined in claim 1.

16. A syringe barrel, comprising the composition as defined in claim 1.

17. Composition according to claim 11, wherein the $C_3$-$C_{10}$ alpha-olefin is one of 1-propylene, 1-butene, 1-hexene and 1-octene.

18. Composition according to claim 11, wherein the $C_3$-$C_{10}$ alpha-olefin is 1-butene or 1-hexene.

19. Composition according to claim 11, wherein the $C_3$-$C_{10}$ alpha-olefin is 1-hexene.

* * * * *